(12) United States Patent
Pfeiffer et al.

(10) Patent No.: US 7,830,512 B2
(45) Date of Patent: Nov. 9, 2010

(54) SYSTEM AND METHOD FOR CONTROLLING INTENSITY OF A BEAM OF ELECTROMAGNETIC RADIATION IN ELLIPSOMETERS AND POLARIMETERS

(75) Inventors: Galen L. Pfeiffer, Lincoln, NE (US); Martin M. Liphardt, Lincoln, NE (US)

(73) Assignee: J.A. Woollam Co., Inc., Lincoln, NE (US)

( * ) Notice: Subject to any disclaimer, the term of this patent is extended or adjusted under 35 U.S.C. 154(b) by 491 days.

(21) Appl. No.: 12/075,956

(22) Filed: Mar. 14, 2008

(65) Prior Publication Data

US 2009/0231700 A1 Sep. 17, 2009

(51) Int. Cl.
*G01J 4/00* (2006.01)
(52) U.S. Cl. .................................................. 356/368
(58) Field of Classification Search .................. None
See application file for complete search history.

(56) References Cited

U.S. PATENT DOCUMENTS

| | | | | |
|---|---|---|---|---|
| 3,880,524 A * | 4/1975 | Dill et al. | | 356/369 |
| 4,097,110 A | 6/1978 | Carey | | 350/149 |
| 5,303,709 A | 4/1994 | Dreher et al. | | 128/665 |
| 5,657,126 A * | 8/1997 | Ducharme et al. | | 356/369 |
| 5,787,890 A | 8/1998 | Reiter et al. | | 128/665 |
| 6,112,114 A | 8/2000 | Dreher | | 600/476 |
| 6,693,711 B1 | 2/2004 | Leger et al. | | 356/369 |
| 6,798,511 B1 | 9/2004 | Zhan et al. | | 356/369 |
| 6,914,675 B1 * | 7/2005 | Drevillon | | 356/369 |
| 6,934,024 B2 | 8/2005 | Zhan et al. | | 356/369 |
| 7,061,561 B2 | 6/2006 | Silverstein et al. | | 349/117 |
| 7,083,835 B2 | 8/2006 | Elman et al. | | 428/113 |
| 7,163,724 B2 | 1/2007 | Elman et al. | | 428/113 |
| 7,170,574 B2 | 1/2007 | Tan et al. | | 349/117 |
| 7,211,304 B2 | 5/2007 | Elman et al. | | 428/113 |
| 7,221,420 B2 | 5/2007 | Elman et al. | | 428/113 |
| 7,236,221 B2 | 6/2007 | Ishikawa et al. | | 349/119 |
| 7,259,844 B2 * | 8/2007 | Fairley et al. | | 356/369 |
| 2002/0091323 A1 | 7/2002 | Dreher | | |
| 2003/0227623 A1 | 12/2003 | Zhan et al. | | |
| 2004/0125373 A1 * | 7/2004 | Oldenbourg et al. | | 356/364 |
| 2004/0179158 A1 | 9/2004 | Silverstein et al. | | |
| 2004/0189992 A9 | 9/2004 | Zhan et al. | | |
| 2004/0208350 A1 | 10/2004 | Rea et al. | | |
| 2005/0002032 A1 * | 1/2005 | Wijntjes et al. | | 356/364 |
| 2005/0024561 A1 | 2/2005 | Elman et al. | | |
| 2005/0128391 A1 | 6/2005 | Tan et al. | | |
| 2005/0270458 A1 | 12/2005 | Ishikawa et al. | | |
| 2005/0270459 A1 | 12/2005 | Elman et al. | | |
| 2005/0286001 A1 | 12/2005 | Elman et al. | | |
| 2006/0099135 A1 | 5/2006 | Yodh et al. | | |
| 2006/0115640 A1 | 6/2006 | Yodh et al. | | |
| 2006/0141466 A1 | 6/2006 | Pinet et al. | | |
| 2006/0193975 A1 | 8/2006 | Elman et al. | | |
| 2006/0203164 A1 | 9/2006 | Silverstein et al. | | |
| 2006/0215158 A1 | 9/2006 | Saitoh | | |
| 2007/0097365 A1 * | 5/2007 | Laiacano et al. | | 356/322 |
| 2007/0247622 A1 * | 10/2007 | Sun | | 356/364 |

* cited by examiner

*Primary Examiner*—Gregory J Toatley
*Assistant Examiner*—Juan D Valentin
(74) *Attorney, Agent, or Firm*—James D. Welch

(57) ABSTRACT

An ellipsometer or polarimeter system and method for controlling intensity of an electromagnetic beam over a spectrum of wavelengths by applying control (P2) and beam (P) polarizers, optionally in combination with an intervening and control compensator (C).

13 Claims, 2 Drawing Sheets

SYSTEM AND METHOD FOR CONTROLLING INTENSITY OF A BEAM OF ELECTROMAGNETIC RADIATION IN ELLIPSOMETERS AND POLARIMETERS

BACKGROUND

It is known that sources of electromagnetic radiation provide non-constant output intensity vs. wavelength characteristics. Further, it is known that detectors of electromagnetic radiation become saturated when too high an intensity is input thereto. Where the intensity of one or more a wavelengths in a spectrum of wavelengths is high enough to saturate a detector, one approach is to attenuate the intensity of all wavelengths. This can be accomplished by a Neutral density filter. Neutral density filters, however, do not pass UV wavelengths and problems can develop using this approach in that reducing the intensity of the highest intensity wavelengths causes reduction of the intensity of other wavelengths below that which a detector can detect. It is also known to cause a beam to reflect off, for instance, a silicon substrate with an oxide on its surface, to provide emphasized IR and UV wavelength intensities with respect to Visible wavelengths, but across the board attenuation is typically not realized by this approach. Another approach to generally reducing intensity is to pass a beam of electromagnetic radiation through an iris which can be reduced, in opening size, however, cross-sectional non-uniformity in the beam can lead to non-uniform results when this approach is used because of varying placement of the iris in the beam.

It is also disclosed that ellipsometers and polarimeters and the like typically comprise a source of a beam of electromagnetic radiation, a beam polarizer, a beam analyzer and a detector arranged so that a beam provided by the source passes through the polarizer, impinges on a sample and the passes through the analyzer and into the detector. The beam polarizer sets a polarization state in said beam which is changed by interaction with a sample, and the analyzer selects polarization states which are passed to the detector for analysis.

As the present invention finds non-limiting application in the investigation of non-specular depolarizing samples, it is noted that non-specular refers to reflections which are not "mirror-like", and depolarizing samples are characterized by a depolarization parameter defined by 1.0 minus the square root of the sum of the squares of:

$$\% DEP = 1 - \sqrt{N^2 + C^2 + S^2}$$

where:

$N = \cos(2\psi)$;

$C = \sin(2\psi) \cos(\Delta)$; and $S = \sin(2\psi) \sin(\Delta)$.

and $\psi$ and $\Delta$ are defined by the well known ellipsometry beam orthogonal component ratio equation:

$$\frac{r_p}{r_s} = \rho = \tan\Psi \cdot \exp(i \cdot \Delta)$$

As the system of the present invention includes "crossed-polarizers", U.S. Patents and Published Applications were identified which include the terms "crossed-polarizer" and "ellipsometry" or "ellipsometer", and are:

Patents:

| | | | |
|---|---|---|---|
| 7,236,221; | 7,221,420; | 7,211,304; | 7,163,724; |
| 7,083,835; | 7,061,561; | 6,934,024; | 6,798,511; |
| 6,693,711; | 6,112,114; | 5,787,890; | 5,303,709; |
| 4,097,110; | 7,170,574; | | |

Published Applications:

| | | |
|---|---|---|
| 2006/0215158; | 2006/0203164; | 2006/0193975; |
| 2005/0286001; | 2005/0270459; | 2005/0270458; |
| 2005/0024561; | 2004/0189992; | 2004/0179158; |
| 2003/0227623; | 2003/0227623; | 2002/0091323; |
| 2006/0141466; | 2006/0115640; | 2006/0099135; |
| 2005/0270458; | 2005/0128391; | 2004/0208350; |
| 2004/0189992; | 2003/0227623; | 2002/0091323. |

It is believed that the foregoing identified prior art is the most relevant to be found and has as its major thrust the application of conventional ellipsometry to the measurement of various parameters such as are common to samples which demonstrate, for instance, low specular reflectance and/or which are depolarizing, (eg. solar cells). Even in view of the prior art, however, need remains for improved systems and improved methodology which better enable application of ellipsometry to the investigation of sample characterizing parameters of samples which, for instance, demonstrate low specular reflectance and/or which are depolarizing.

DISCLOSURE OF THE INVENTION

The present invention is disclosed in the context of an ellipsometer or polarimeter and the like which comprises a source of a beam of electromagnetic radiation, a beam polarizer, an analyzer, a detector, and optionally at least one system compensator positioned between the beam polarizer and the analyzer. The present invention adds a control polarizer, and optionally a sequentially located control compensator, between the source of a beam of electromagnetic radiation and the beam polarizer in ellipsometer or polarimeter system, such that a beam of electromagnetic radiation provided by the source thereof passes through the control polarizer and optionally, when present, the control compensator, then through the beam polarizer and impinge on a sample, interact therewith, (eg. typically reflect therefrom but possibly transmit therethrough), and then pass through the analyzer and into the detector. Again, the control polarizer is positioned before the beam polarizer and in use is rotated with respect to the beam polarizer to substantially uniformly attenuate the intensity of all wavelengths which pass through said beam polarizer. And again, the present invention can also position a control compensator between the control and beam polarizers, which control compensator can be applied to cause selective attenuation of some wavelengths in the spectrum more than others.

The present invention then comprises a system for controlling the intensity of a beam of electromagnetic radiation as a function of wavelength, comprising a source of a polychromatic beam of electromagnetic radiation and a sequence of control and beam polarizers, said control and beam polarizers being rotatable with respect to one another. In use the beam polarizer is caused to set a polarization state in a beam exiting therefrom, and the control polarizer is rotated with respect to said beam polarizer to substantially uniformly control the intensity of the beam exiting the beam polarizer over a spectrum of wavelengths. The system can further comprise a compensator between said control and beam polarizers which serves to cause selective attenuation of some wavelengths more than others in said spectrum of wavelengths. Said system can further comprise an analyzer and a detector such that in use the polarized beam exiting said beam polarizer interacts with a sample and then passes through said analyzer and into said detector, and said system is an ellipsometer or polarimeter. Said system can further comprise at least one system compensator between said beam polarizer and said analyzer. (It is noted that where a Berek-type control compensator, which has its optical axis perpendicular to a surface thereof which a beam enters is used, the terminology "rotation" thereof should be interpreted to mean a tipping thereof to position the optical axis other than parallel to the locus of the beam which passes therethrough, and where the control compensator has its optical axis in the plane of a surface thereof which a beam enters is used, rotation should be interpreted to means an actual rotation about a perpendicular to said surface).

A method of controlling the intensity of a beam of electromagnetism over a spectral range, comprising the steps of:

a) providing a system for controlling the intensity of a beam of electromagnetic radiation as described above;

b) setting a beam polarization state with the beam polarizer and rotating the control polarizer with respect thereto to control the intensity.

Said method can further comprise providing a compensator between said control and beam polarizers which serves to selectively attenuate the intensity of some wavelengths in said spectrum more than others.

A typical procedure provides that the control and beam polarizers be rotated with respect to one another so that less intensity than is possible from the source, proceeds to the sample. This might be approached using a highly reflective test sample, for instance and the control polarizer adjusted to provide a non-saturating signal to the detector. When a less reflective sample is investigated, the control and beam polarizers can then be rotated with respect to one another so that greater intensity is applied to the less reflective sample. When present, the control compensator can be also be adjusted to further control the intensity vs. wavelength characteristic of a beam impinging on the sample.

For clarity, it is recited that the present invention comprises an ellipsometer or polarimeter system comprising means for controlling the intensity of a beam of electromagnetic radiation as a function of wavelength comprising:

a source of a polychromatic beam of electromagnetic radiation;

a sequence of a control polarizer, a control compensator and beam polarizer;

said control and beam polarizers and said control compensator being rotatable with respect to one another, said system further comprising:

an analyzer; and a detector;

such that in use the polarized beam provided by said source which exits said beam polarizer, interacts with a sample and then passes through said analyzer and into said detector;

such that in use the beam polarizer is caused to set a polarization state in a beam exiting therefrom, and the control polarizer and control compensator can be rotated with respect to said beam polarizer to substantially uniformly control the intensity of the beam exiting the beam polarizer over a spectrum of wavelengths.

Said ellipsometer or polarimeter system can further comprise at least one system compensator between said beam polarizer and said analyzer.

The present invention also comprises a method of controlling the intensity of a beam of electromagnetism over a spectral range, comprising the steps of:

a) providing an ellipsometer or polarimeter system as described just above;

b) setting a beam polarization state with the beam polarizer and rotating the control polarizer and/or control compensator with respect thereto to control the intensity of said beam over the spectrum of wavelengths.

The invention will be better understood by reference to the Detailed Description Section of this Specification, in conjunction with the Drawings.

DETAILED DESCRIPTION

Figure 1:
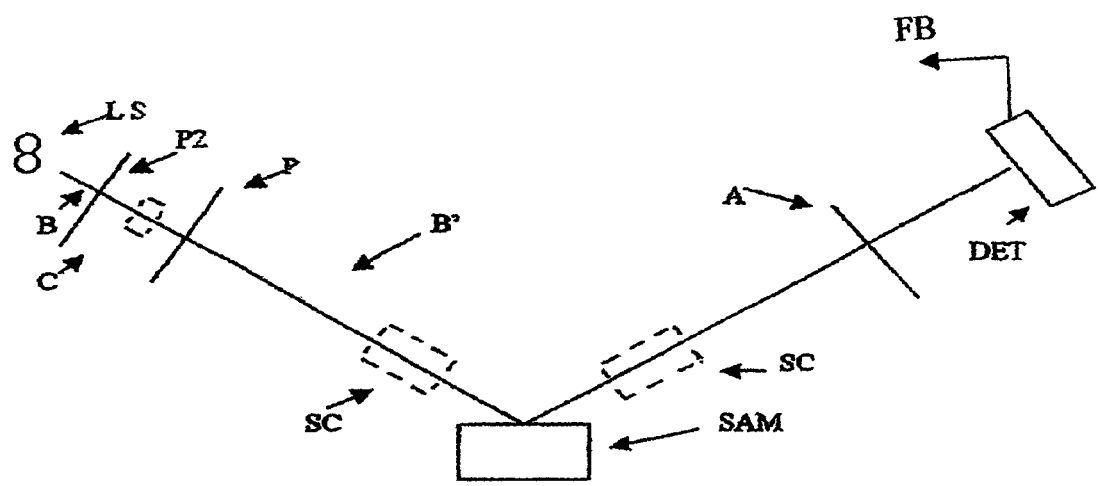
FIG. 1 shows a system for controlling the intensity of a beam of electromagnetic radiation comprising a Source (LS) of a Beam (B) of Electromagnetism, a Control Polarizer (P2), an optional Control Compensator (C), a Beam Polarizer (P), a Sample (SAM), an Analyzer (A) and a Detector (DET).
Figure 2:
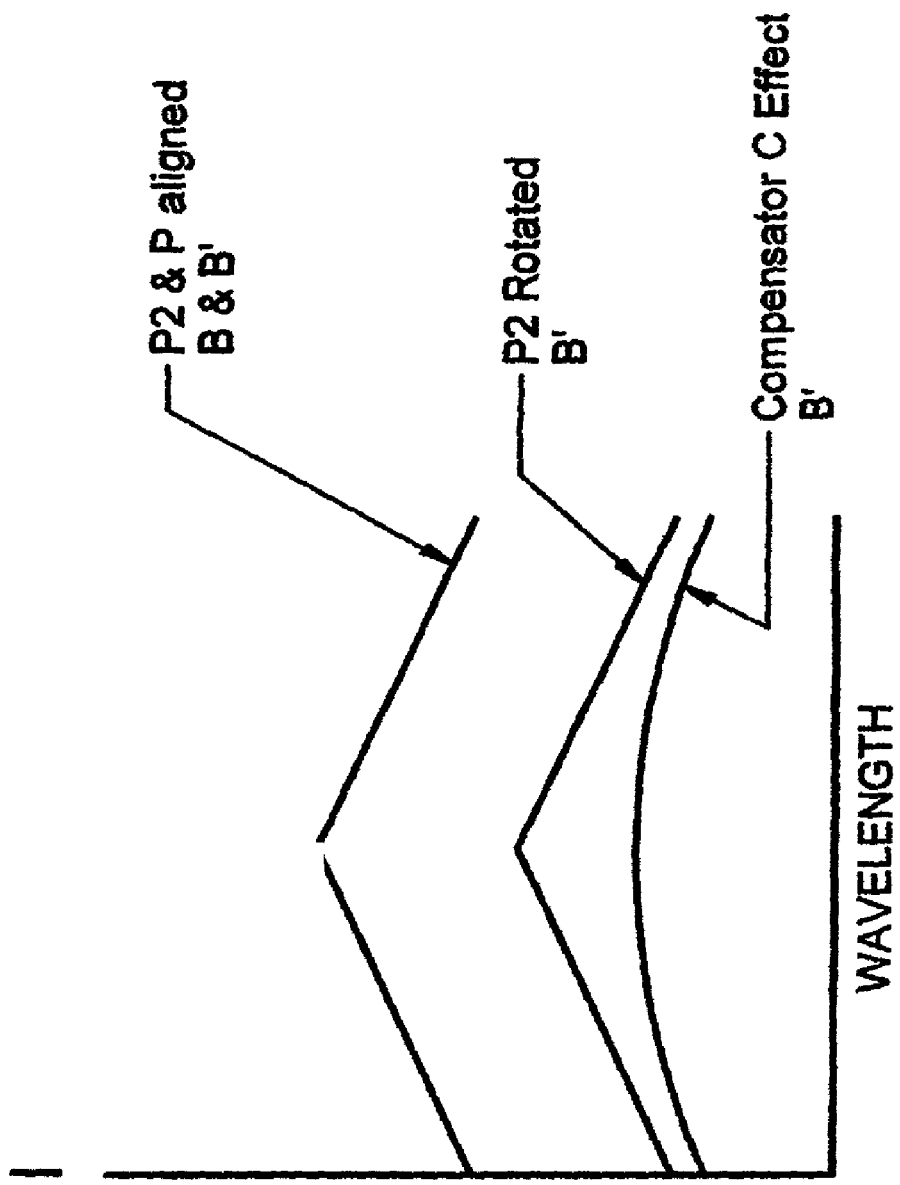
FIG. 2 shows an arbitrary demonstrative effect on Intensity (I) of a Beam (B') as compared to the Intensity of Beam (B) provided by a Source (LS) in FIG. 1.

FIG. 1 shows a Source (LS) of a Beam (B) of Electromagnetism, a Control Polarizer (P2), an optional Compensator (C), a Beam Polarizer (P), a Sample (SAM), an Analyzer (A) and a Detector (DET). FIG. 2 shows an arbitrary demonstrative effect on Intensity (I) of a Beam (B') as compared to the Intensity of Beam (B) provided by a Source (LS). Note the baseline Intensity (I) when said Control and Beam Polarizers (P2) and (P) aligned, and that rotating the Control Polarizer (P2) with respect to the beam Polarizer (P) has a uniform effect over the Wavelength Spectrum. Adding a Control Compensator (C) can cause selective increased attenuation of the mid-wavelength region and provide a more uniform Intensity Spectrum. Note also that at least one System Compensator (SC) can be incorporated into the system. (It is noted that where a Berek-type control compensator, which has its optical axis perpendicular to a surface thereof which a beam enters is used, the terminology "rotation" thereof should be interpreted to mean a tipping thereof to position the optical axis other than parallel to the locus of the beam which passes therethrough, and where the control compensator has its optical axis in the plane of a surface thereof which a beam enters is used, rotation should be interpreted to means an actual rotation about a perpendicular to said-surface).

Finally, it is disclosed that rotation of the control polarizer or compensator can be automated, optionally via a signal in a feedback circuit (FB).

Having hereby disclosed the subject matter of the present invention, it should be obvious that many modifications, substitutions, and variations of the present invention are possible in view of the teachings. It is therefore to be understood that the invention may be practiced other than as specifically described, and should be limited in its breadth and scope only by the Claims.

We claim:

1. A system for controlling the intensity of a beam of electromagnetic radiation as a function of wavelength comprising a source (LS) of a beam of polychromatic electromagnetic radiation and a sequence of control (P2) polarizer and a beam polarizer (P), said control (P2) and beam (P) polarizers being rotatable with respect to one another, such that in use the beam (P) polarizer is caused to set a polarization state in a beam exiting therefrom, and the control (P2) polarizer is rotated with respect to said beam (P) polarizer to substantially uniformly control the intensity of wavelengths in the beam exiting the beam polarizer (P) over a spectrum of wavelengths;

said system further comprising a control compensator (C) between said control (P2) polarizer and beam (P) polarizer which can be applied to cause selective attenuation of some wavelengths more than others in said spectrum of wavelengths.

2. A system as in claim 1 which further comprises an analyzer (A) and a detector (DET) such that in use the polarized beam exiting said beam (P) polarizer interacts with a sample (SAM) and then passes through said analyzer (A) and into said detector (DET), and said system is an ellipsometer or polarimeter.

3. A system as in claim 1 which further comprises a system compensator (SC) between said beam polarizer (P) and said analyzer (A).

4. A system as in claim 1 in which the rotation of the control (C) compensator is automated.

5. A method as in claim 4 in which the rotation of control (C) compensator is automated via a feedback circuit.

6. A method of controlling the intensity of a beam of electromagnetism over a spectral range, comprising the steps of:

a) providing a system for controlling the intensity of a beam of electromagnetic radiation as a function of wavelength comprising a source (LS) of a beam of polychromatic electromagnetic radiation and a sequence of a control (P2) polarizer and a beam (P) polarizer, said control (P2) and beam (P) polarizers being rotatable with respect to one another, such that in use the beam (P) polarizer is caused to set a polarization state in a beam exiting therefrom, and the control (P2) polarizer is rotated with respect to said beam (P) polarizer to substantially uniformly control the intensity of wavelengths in the beam exiting the beam (P) polarizer over a spectrum of wavelengths;

further comprising a control compensator (C) between said control (P2) polarizer and beam (P) polarizer, which can be applied to cause selective attenuation of some wavelengths more than others in said spectrum of wavelengths;

b) setting a beam polarization state with the beam (P) polarizer and rotating the control (P2) polarizer with respect thereto to substantially uniformly control the intensity of wavelengths in said beam over the spectrum of wavelengths, and optionally applying said control compensator (C) to selectively attenuate some wavelengths of said spectrum of wavelengths more than others.

7. A method as in claim 6 in which the rotation of control (P2) polarizer is automated.

8. A method as in claim 7 in which the rotation of the control (P2) polarizer is automated via a feedback circuit.

9. An ellipsometer or polarimeter system comprising means for controlling the intensity of wavelengths in a beam of electromagnetic radiation as a function of wavelength comprising:

a source (LS) of a beam of polychromatic electromagnetic radiation;

a sequence of a control (P2) polarizer and a beam polarizer (P);

said control (P2) and beam (P) polarizers being rotatable with respect to one another, said system further comprising:

an analyzer (A);

and a detector (DET);

such that in use the beam provided by said source (LS) which exits said beam (P) polarizer in a polarized state, interacts with a sample (SAM) and then passes through said analyzer (A) and into said detector (DET); and such that in use the beam (P) polarizer is caused to set a polarization state in a beam exiting therefrom, and the control (P2) polarizer can be rotated with respect to said beam (P) polarizer to substantially uniformly control the intensity of wavelengths in the beam exiting the beam polarizer (P) over a spectrum of wavelengths.

10. An ellipsometer or polarimeter system as in claim 9, which further comprises at least one system compensator (SC) between said beam polarizer (P) and said analyzer (A).

11. An ellipsometer or polarimeter system as in claim 9 which further comprises a control compensator (C) between said beam (P) and control (P2) polarizers, and further applying said control compensator (C) to selectively attenuate the intensity of some wavelengths in said spectrum of wavelengths more than others.

12. A method of controlling the intensity of wavelengths in a beam of electromagnetism over a spectral range, comprising the steps of:

a) providing an ellipsometer or polarimeter system comprising means for controlling the intensity of wavelengths in a beam of electromagnetic radiation as a function of wavelength comprising:

a source (LS) of a beam of polychromatic electromagnetic radiation;

a sequence of a control (P2) polarizer and a beam polarizer (P);

said control (P2) and beam (P) polarizers and being rotatable with respect to one another, said system further comprising:

an analyzer (A); and a detector (DET);

such that in use the beam provided by said source (LS) which exits said beam (P) polarizer, interacts with a sample (SAM) and then passes through said analyzer (A) and into said detector (DET);

such that in use the beam (P) polarizer is caused to set a polarization state in a beam exiting therefrom, and the control (P2) polarizer can be rotated with respect to said beam (P) polarizer to substantially uniformly control the intensity of the beam exiting the beam polarizer (P) over a spectrum of wavelengths; b) setting a beam polarization state with the beam (P) polarizer and rotating the control (P2) polarizer and/or control compensator (C) with respect thereto to control the intensity of said beam over the spectrum of wavelengths;

b) setting a beam polarization state with the beam (P) polarizer and rotating the control (P2) polarizer with respect thereto to control the intensity of said beam over the spectrum of wavelengths.

13. A method as in claim 12 in which the ellipsomster or polarimeter system provided in step a) further comprises a control compensator (C) between said beam (P) and control (P2) polarizers, and in which step b) further comprises applying said control compensator (C) to selectively attenuate the intensity of some wavelengths in said spectrum more than others.

* * * * *